US00PP13052P2

(12) United States Plant Patent
Garabedian et al.

(10) Patent No.: US PP13,052 P2
(45) Date of Patent: Oct. 8, 2002

(54) VARIETY OF PLUM TREE NAMED 'ROSY JEWEL'

(76) Inventors: John M. Garabedian, deceased, late of Fresno, CA (US); by Malcolm H. Stewart, executor, 3445 N. Cedar Ave., Fresno, CA (US) 93726; by Edward A. Miller, executor, 3445 N. Cedar Ave., Fresno, CA (US) 93726; by Michael J. Harrington, executor, 3445 N. Cedar Ave., Fresno, CA (US) 93726

( * ) Notice: Subject to any disclaimer, the term of this patent is extended or adjusted under 35 U.S.C. 154(b) by 0 days.

(21) Appl. No.: 09/595,443

(22) Filed: Jun. 16, 2000

Related U.S. Application Data

(63) Continuation of application No. 09/152,913, filed on Sep. 14, 1998, now abandoned.

(51) Int. Cl.[7] ..... A01H 5/00
(52) U.S. Cl. ..... Plt./184
(58) Field of Search ..... Plt./184

(56) References Cited

PUBLICATIONS

UPOV ROM GTITM Computer Database, GTI JOUVE Retrieval Software, 2001/02, citation for 'Rosy Jewel'.*

* cited by examiner

*Primary Examiner*—Bruce R. Campell
*Assistant Examiner*—Annette H. Para
(74) *Attorney, Agent, or Firm*—Fitzpatrick, Cella, Harper, & Scinto

(57) ABSTRACT

A new variety of plum tree which is mature for harvesting and shipment from the last week of May to the first week of June in the San Joaquin Valley of Central California with a substantially dark burgundy skin color.

1 Drawing Sheet

This application is a continuation of application Ser. No. 09/152,913, filed on Sep. 14, 1998, now abandoned.

BACKGROUND OF THE NEW VARIETY

In the development of new varieties of fruit trees, a premium is usually placed upon those varieties which have fruit which ripens early or late in the growing season when there are few competing varieties available. These varieties, which typically have poor color, size, flavor or poor handling or shipping characteristics may not have reasonable or good acceptance by the consumer. Thus, any early or late maturing new variety free from these deficiencies will have widespread acceptance in the fresh market.

The present invention relates to a 7 year old new and distinct variety of plum tree, known varietally hereafter as 'Rosy Jewel'. This new variety produces a semi-freestone fruit having a dark red skin color over 40% of the fruit. The fruit matures early in the growing season and is ready for commercial harvest in late May to early June.

ORIGIN AND ASEXUAL REPRODUCTION OF THE NEW VARIETY

The present variety of plum tree was discovered by the inventor as an open pollinated seedling in a plum planting located at the corner of Kings Canyon Road and Fowler Avenue in Fresno, Calif. in the San Joaquin Valley of Central California. The new variety was first asexually reproduced in the winter of 1997 at the plum planting at Fowler Avenue and Belmont Avenue in Fresno, Calif., by bud grafting onto Nemaguard rootstock. The asexually reproduced tree produced fruit in late May of 1998 of the new variety and confirmed that the parent and the progeny were identical in all respects. A second propagation was made (4 acres) at the N/S Harvey Avenue, ½ mile E/S Fowler Avenue on Nemaguard rootstock.

SUMMARY OF THE NEW VARIETY

The 'Rosy Jewel' plum tree is characterized by producing a semi-freestone fruit which has a dark burgundy skin color over 90% of the fruit with heavy bloom, which is ripe for commercial harvest and shipment in the last week of May to the first week of June in the San Joaquin Valley of Central California. The flesh of this plum fruit is very pale, near water green (P1. 19 C2), except near the pit where it is even lighter in color (P1. 19 C1).

BRIEF DESCRIPTION OF THE DRAWING

The drawing is a colored photograph showing fruit of the present invention with various degrees of blush, two fruit showing the stem end, two fruit displaying the blossom end, two fruit displaying the sutures, two fruit showing the ventrose side, one fruit cut in half showing the pit well and flesh, a stone (P11) and the upper and lower surfaces of the leaves.

DETAILED DESCRIPTION

Referring to more specific pomological details of this new and distinct variety of plum tree, the following description has been observed under the ecological conditions prevailing at the orchard of origin which is located in Fresno in the San Joaquin Valley of Central California. All major color code designations are by reference to the Dictionary of Color by Maerz and Paul, first edition, 1930. Common color names are also occasionally used.

Tree:

*Varietal name.*—'Rosy Jewel'.

*Botanical name.*—*Prunus domestica.*

*Size.*—Generally 10–12 feet in height with a lateral spread of 12–15 feet.
*Vigor.*—Moderate — New growth in year 2001 was 2.5 to 3 feet.
*Form.*—Upright with open vased system of training.
*Productivity.*—Productive — About 350 24 lb. boxes/acre.
*Regularity of bearing.*—Regular under the ecological conditions of the Central California San Joaquin Valley.

Trunk:
*Size.*—Medium — 20 inches in circumference, 14 inches above ground level at 7 years old.
*Surface texture.*—Somewhat shaggy.
*Color.*—Mauve castor (P1. 55 E2).
*Lenticels.*—Numerous, medium size.

Branches:
*Size.*—Medium — 11 inches in circumference at 30 inches above ground.
*Color of mature branches.*—Brown (P1. 55 E5) with angle approximately 38 degrees.
*Color of immature branches.*—Box green (P1. 23 H3).

Leaves:
*Size.*—Medium.
*Form.*—Ovate.
*Length.*—105–124 mm (4.13–4.89 inches).
Width.—43–60 mm (1.69–2.36 inches).
*Thickness.*—Average for plums.
*Color.*—Upper surface — Cossack green (P1. 24 I7). Lower surface — Close to Guette green (P1. 22 J8).
*Marginal form.*—Double serrate.
*Glands.*—2, globular in shape, small, green in October at base of leaves.
*Petiole.*—13–16 mm long (0.51 to 0.63 inch) — 1.5 mm wide (0.06 inch) — Color: Kress green (P1. 22 K6).
*Stipules.*—0–2, small.

Flower buds:
*Shape.*—Conic.
*Size.*—Length — 5 mm (0.20 inch) — Width — 5 mm (0.20 inch).
*Calyx.*—5 sepals — brownish — Length — 5 mm (0.20 inch).

Flowers:
*Date of first bloom.*—February 18 — heavy, 100% by February 28.
*Size.*—22–25 mm diameter (0.866–0.984 inch).
*Color.*—White.
*Number.*—Borne in clusters of 2–5.
*Petals.*—Length — 5–10 mm (0.384 inch) — Width — 15 mm (0.59 inch).
*Petal claw.*—Very small, truncate.
*Margins.*—Undulate with rounded margins.
*Flower pedicels.*—Length — 6 mm (0.236 inch) — Diameter — 1 mm (0.039 inch) — Color — Ocean green (P1. 18 B5).
*Anthers.*—Small — 1.55 mm — Color — Roman ochre (P1. 11 K9).
*Stamen.*—20–25.
*Pistil.*—1 — Length — Small — 10–11 mm (0.394–0.433 inch) — Color — Reed green (P1. 19 D4) — Surface — Slightly pubescent.

Fruit:
*Mature.*—End of May–June in the Fresno area of Central California.
*Size.*—Uniform medium — 3–4 fruit lb.
*Average diameter in the axil plane.*—55–58 mm(2.17–2.28 inches).
*Average diameter transverse in the suture plane.*—55–60 mm (2.17–2.35 inches).
*Average diameter at right angles to suture plane.*—52–60 mm (2.05–2.35 inches).
*Shape.*—Globulate.
*Suture.*—Distinct suture present.
*Ventral surface.*—Rounded, slightly lipped.
*Stem cavity.*—Oval in shape — Length — 12 mm (0.47 inch) — Width — 13 mm (0.51 inch) — Depth — 9 mm (0.351 inch).
*Stem.*—Short, medium — Length — 10–12 mm (0.394–0.446 inch) — Diameter — 2–3 mm.
*Base.*—Rounded.
*Apex.*—Recessed.
*Blush color.*—Harbor blue over nearly 50% of fruit (P1. 38 G6).
*Ground color.*—Eggplant (P1. 48 H12).
*Flesh color.*—Near skin — Water green (P1. 19 C2) — Near pit — P1. 19 C1.
*Color of pit well.*—P1. 10 G5.
*Pit well.*—Length — 24 mm (0.994 inch) — Width — 20 mm (0.787 inch) — Depth — 9 mm (0.351 inch).
*Flavor.*—Slightly subacid, good, mild.
*Aroma.*—Wanting.

Stone:
*Color dry.*—Capucine Y (P1. 9 K8).
*Type.*—Semi-free stone, medium.
*Fibers.*—Few adhering, large.
*Size.*—Length — 24 mm (0.94 inch) — Width — 22 mm (0.866 inch) — Thickness — 8–9 mm (0.315–0.354 inch).
*Apex.*—Slightly pointed.
*Base.*—Slightly truncate.
*Surface.*—Laterally grooved.
*Hilum.*—Narrow and oblong.
*Ventral edge.*—Low winged.
*Dorsal edge.*—Tightly grooved.
*Storage.*—Under cold temperature 33° to 34° F. from 7 to 30 days.
*Shipping.*—Very good.

Although the new variety of plum tree possesses the above-described characteristics resulting from being under the ecological growing conditions prevailing near Fresno, Calif., in the Central San Joaquin Valley of California, it should be understood that variations of the usual magnitude and characteristics may occur due to changes in growing conditions, irrigation, fertilization, pruning, pest control and climate.

I claim:

1. A new and distinct variety of plum tree named 'Rosy Jewel' substantially as described and illustrated.

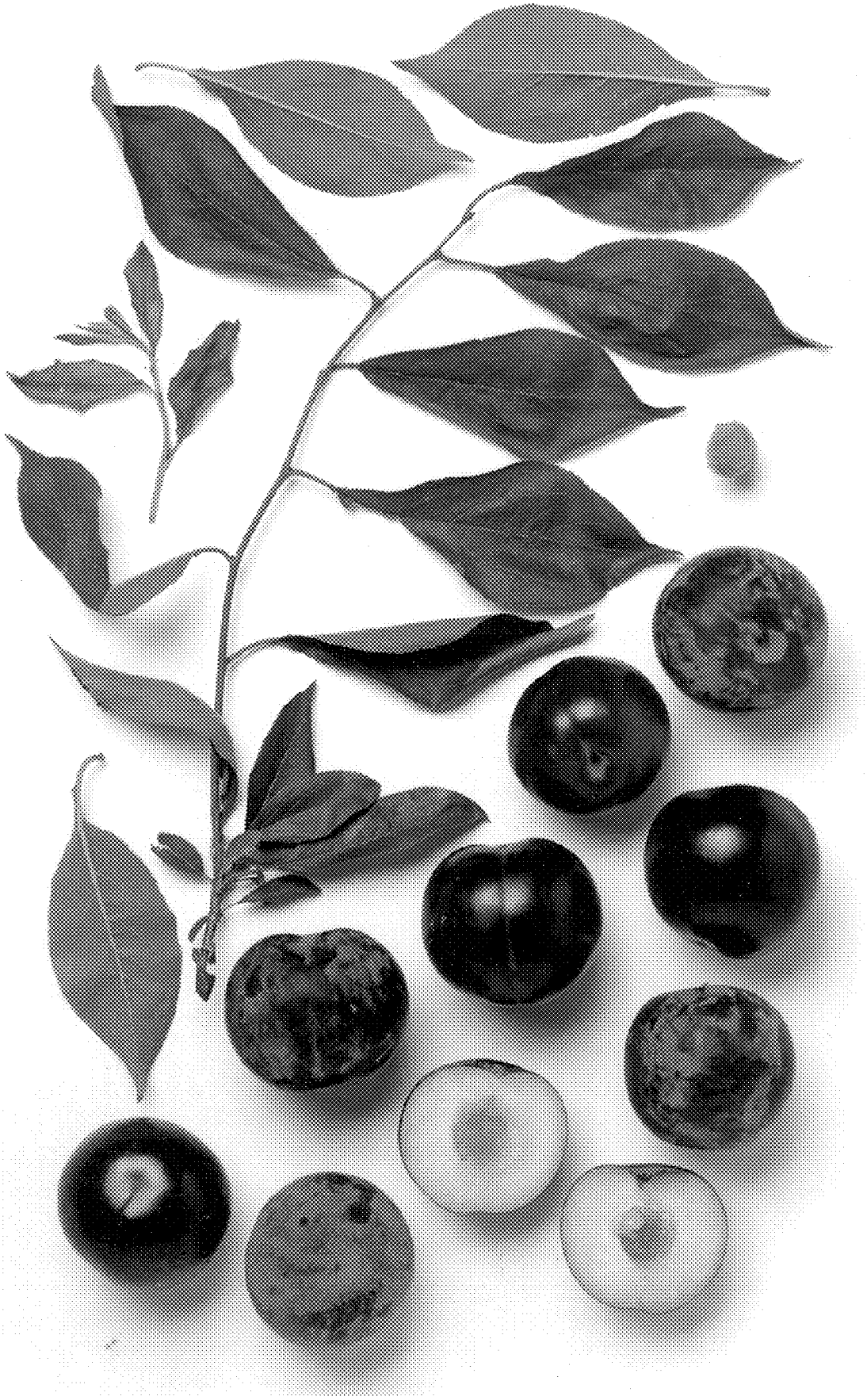

* * * * *